United States Patent
Han et al.

(10) Patent No.: US 9,702,855 B2
(45) Date of Patent: Jul. 11, 2017

(54) ACOUSTIC INTERFACE DEVICE

(71) Applicant: Baker Hughes Incorporated, Houston, TX (US)

(72) Inventors: Wei Han, Sugar Land, TX (US); Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 328 days.

(21) Appl. No.: 14/472,367

(22) Filed: Aug. 29, 2014

(65) Prior Publication Data

US 2016/0061629 A1   Mar. 3, 2016

(51) Int. Cl.
*G01N 29/00* (2006.01)
*G01D 5/12* (2006.01)
*G01N 29/28* (2006.01)

(52) U.S. Cl.
CPC ................................. *G01N 29/28* (2013.01)

(58) Field of Classification Search
CPC ........... G01D 5/12; G01N 29/00; G01N 29/28
USPC .......................................................... 73/658
See application file for complete search history.

(56) References Cited

U.S. PATENT DOCUMENTS

| | | | |
|---|---|---|---|
| 4,320,659 A | 3/1982 | Lynnworth et al. | |
| 4,346,599 A | 8/1982 | McLaughlin et al. | |
| 4,373,197 A | 2/1983 | Gassaway et al. | |
| 4,743,870 A | 5/1988 | Jen et al. | |
| 4,754,645 A | 7/1988 | Piche et al. | |
| 4,779,452 A | 10/1988 | Cohen-Tenoudji et al. | |
| 4,783,997 A | 11/1988 | Lynnworth | |
| 4,862,384 A | 8/1989 | Bujard | |
| 5,159,838 A | 11/1992 | Lynnworth | |
| 5,241,287 A | 8/1993 | Jen | |
| 5,433,112 A | 7/1995 | Piche et al. | |
| 5,606,971 A | 3/1997 | Sarvazyan | |
| 5,814,731 A | 9/1998 | Alexander et al. | |
| 5,828,274 A | 10/1998 | Jen et al. | |
| 5,951,163 A | 9/1999 | Jen et al. | |
| 6,047,602 A | 4/2000 | Lynnworth | |
| 7,124,635 B2 | 10/2006 | Kushibiki et al. | |
| 9,173,633 B2 * | 11/2015 | Sudo .................... | A61B 5/0095 |
| 2002/0193004 A1 | 12/2002 | Boyle et al. | |
| 2004/0254469 A1 * | 12/2004 | Shkarlet ............... | A61B 5/6876 |
| | | | 600/459 |

(Continued)

OTHER PUBLICATIONS

US 8,739,629, 06/2014, Cawley et al. (withdrawn)

(Continued)

*Primary Examiner* — J M Saint Surin
(74) *Attorney, Agent, or Firm* — Hirsch & Westheimer, P.C.

(57) ABSTRACT

A system is provided including an acoustic interface device, configured for coupling to a transducer and to a specimen, the acoustic interface device comprising a material composition having a shear wave attenuation coefficient $\alpha_S$ of at least about 5 dB/cm when subjected to an acoustic signal at a frequency between about 200 to 500 kHz. The acoustic interface device may be formed of polytetrafluoroethylene (Teflon®), a perfluoroalkoxy alkane (PFA), polycarbonate (Lexan®), or polyether ether ketone (PEEK). Methods of using the acoustic interface device with a transducer for ultrasonic measurement of a specimen are also disclosed.

20 Claims, 10 Drawing Sheets

(56) References Cited

U.S. PATENT DOCUMENTS

| | | | |
|---|---|---|---|
| 2006/0028096 A1 | 2/2006 | Kushibiki et al. | |
| 2009/0049918 A1* | 2/2009 | Luo | C08K 7/04 73/627 |
| 2009/0107724 A1 | 4/2009 | Utter et al. | |
| 2011/0242938 A1 | 10/2011 | Garcia-Osuna et al. | |
| 2013/0030723 A1* | 1/2013 | Gao | B29C 45/77 702/50 |
| 2014/0276060 A1* | 9/2014 | Hayashi | A61B 8/14 600/443 |

OTHER PUBLICATIONS

PCT International Search Report and Written Opinion issued in Application No. PCT/US2015/047551 on Dec. 14 2015, 14 pages.
L. C. Lynnworth, Ultrasonic Measurements for Process Control: Theory, Techniques, Applications, 1989, p. 142, Academic Press, Inc., San Diego and London.
H. Sato, I. S. Sacks, T. Murase, G. Muncill and H. Fukuyama, "Attenuation of compressional waves in peridotite measured as a function of temperature at 200 MPa" (Abstract), Pure and Applied Geophysics, Mar. 1, 1988, pp. 433-447, vol. 128, Issue 1-2, Birkhauser Verlag.
I. Ihara, "Ultrasonic Sensing: Fundamentals and its Applications to Nondestructive Evaluation" (draft, pp. 1-20, printed as chapter in Sensors: Advancements in Modeling, Design Issues, Fabrication and Practical Applications, eds. S.C. Mukhopadhyay and R.Y.M. Huang, 2008, pp. 287-305 (vol. 21 of Series: Lecture Notes in Electrical Engineering), Springer, Berlin and Heidelberg).
H.J. McSkimin, "Measurement of Ultrasonic Wave Velocities and Elastic Modulii for Small Solids Specimens at High Temperatures," The Journal of the Acoustical Society of America, Mar. 1959, pp. 287-295, vol. 31, No. 3.
C.K. Jen, L. Piche and J.F. Bussiere, "Long isotropic buffer rods," The Journal of the Acoustical Society of America, Jul. 1990, pp. 23-25, vol. 88, No. 1.
M.V.M.S. Rao and K.J. Prasanna Lakshmi, "Shear-wave propagation in rocks and other lossy media: An experimental study," Current Science, Oct. 25, 2003, pp. 1221-1225, vol. 85, No. 8.

* cited by examiner

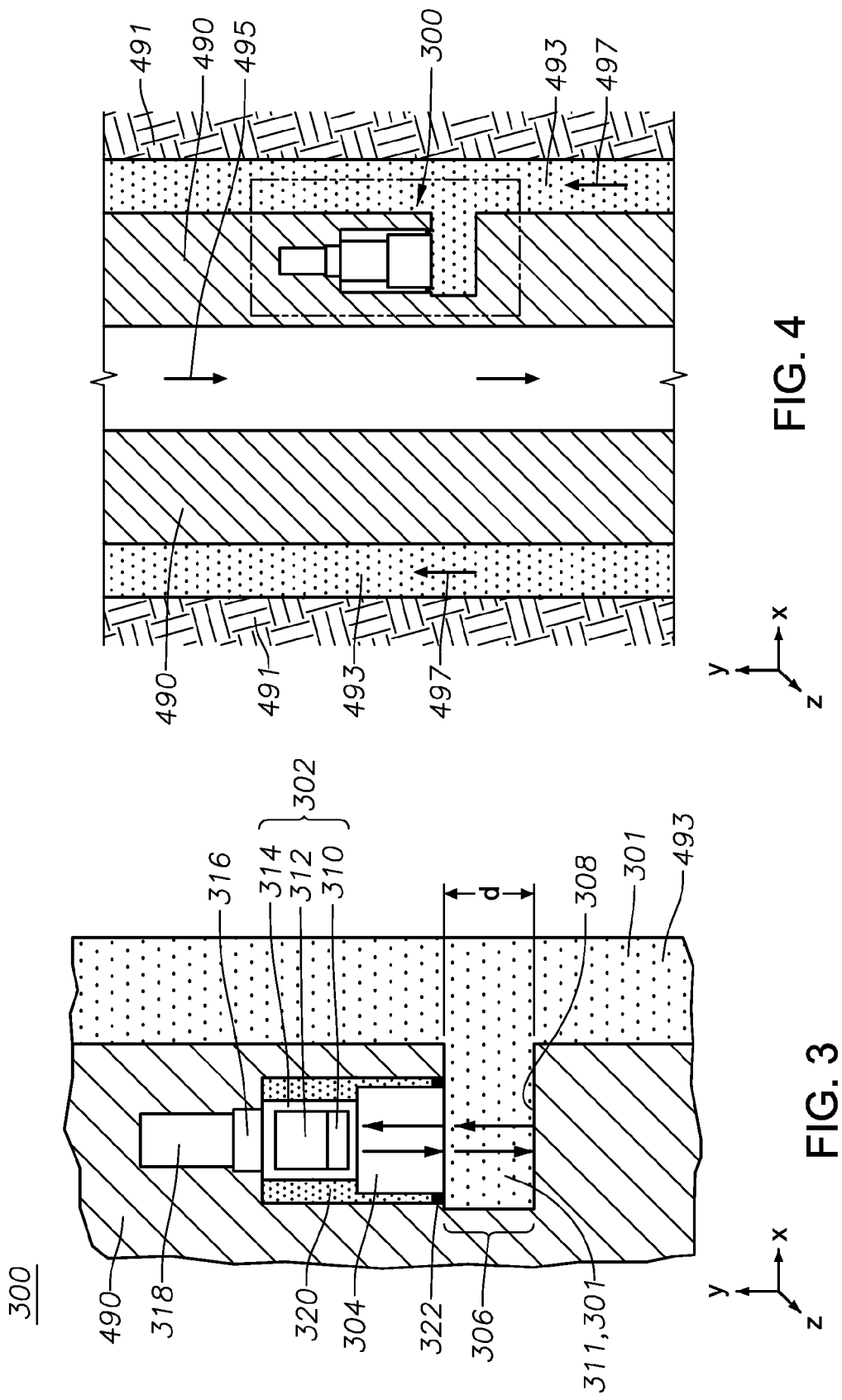

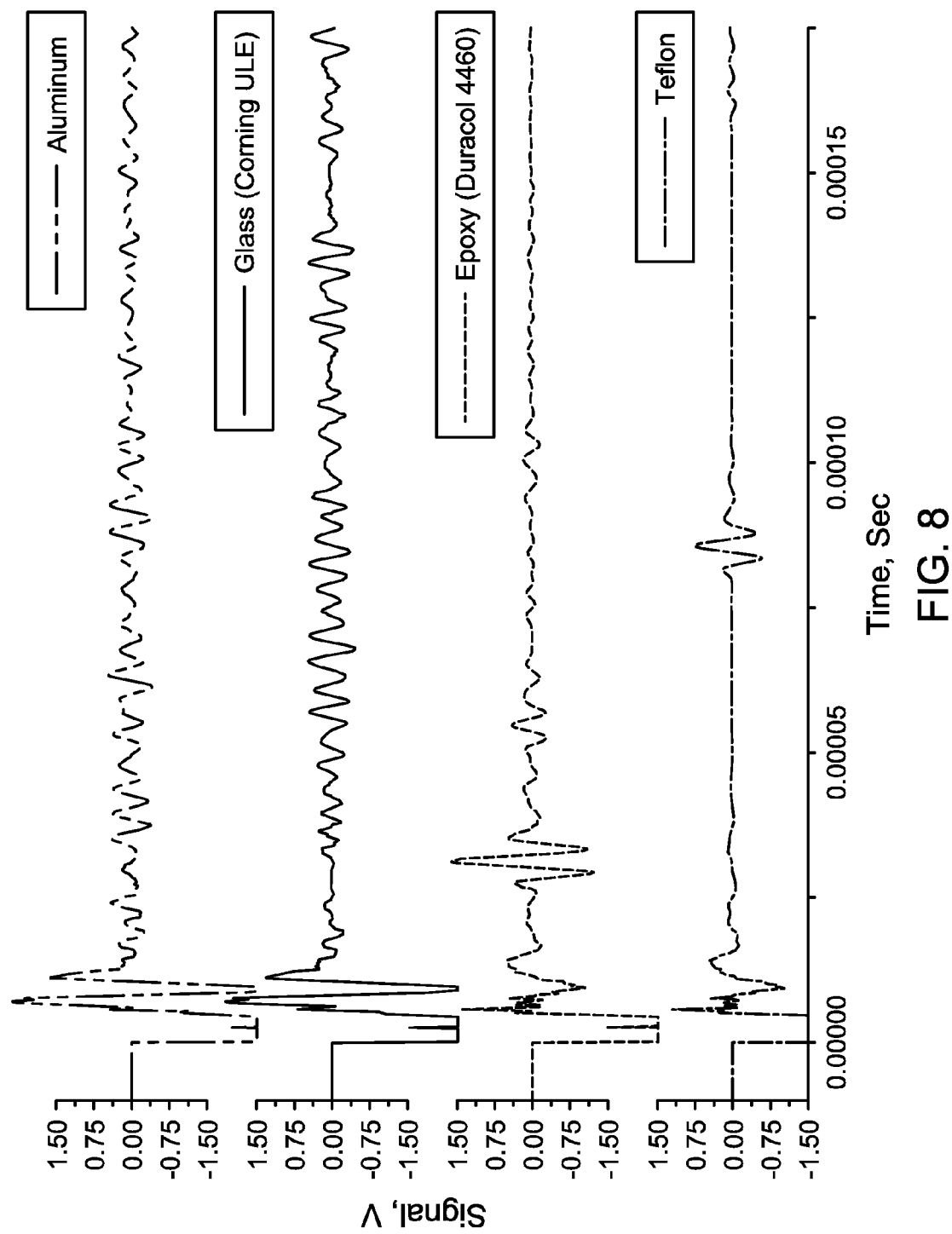

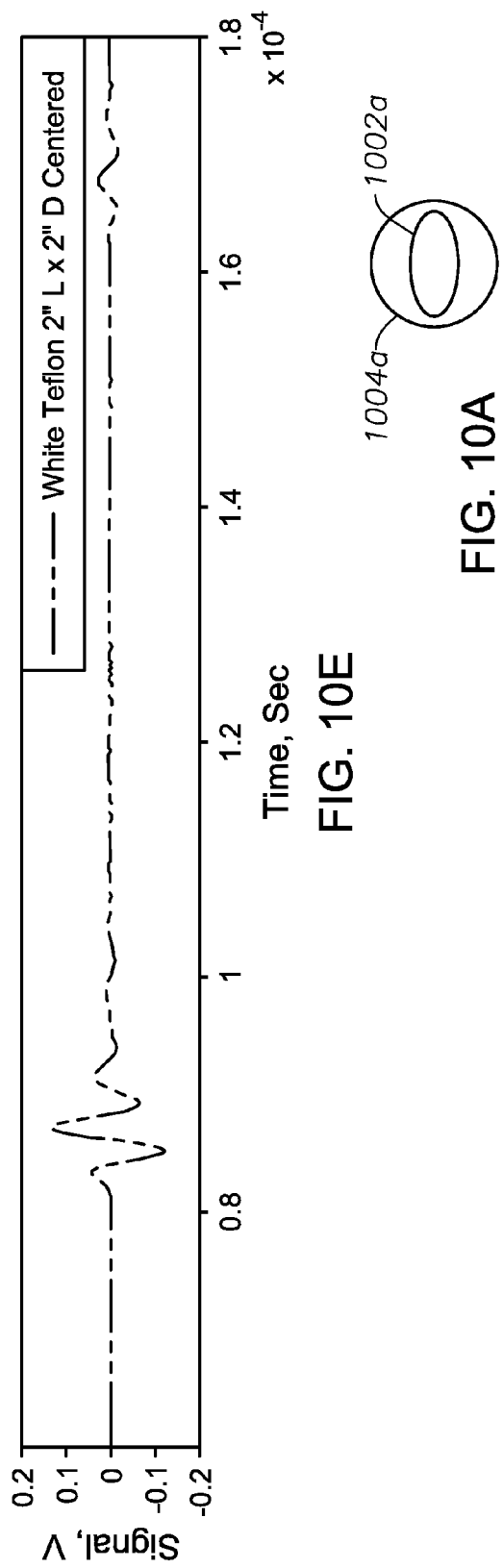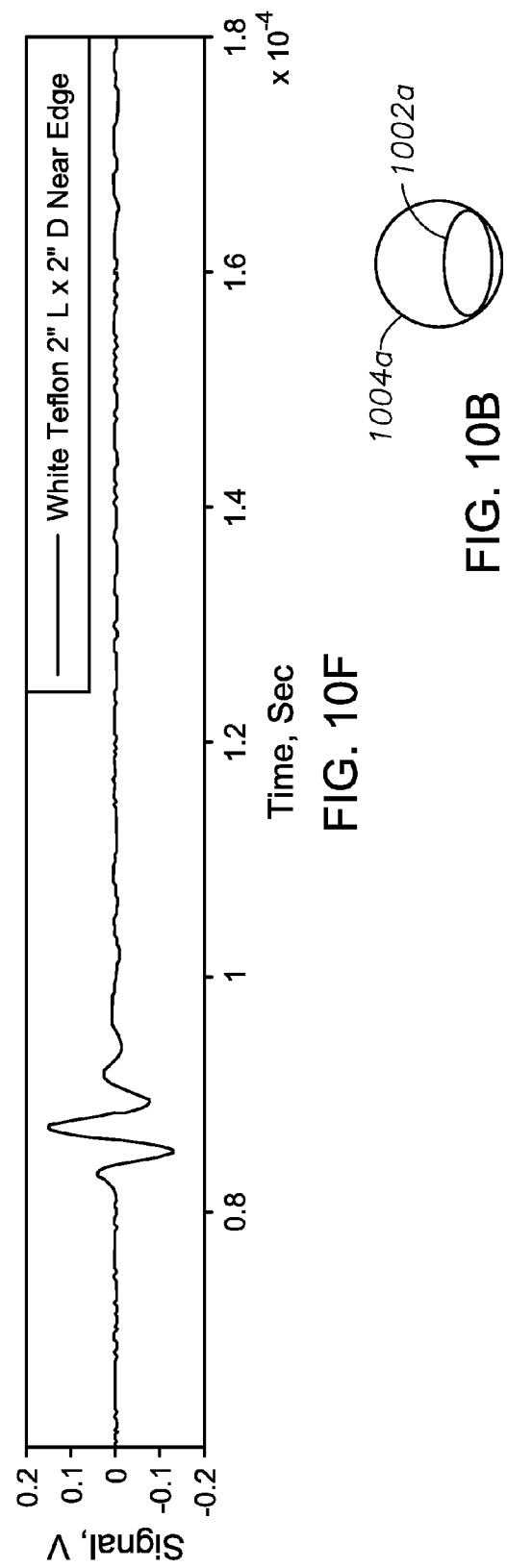

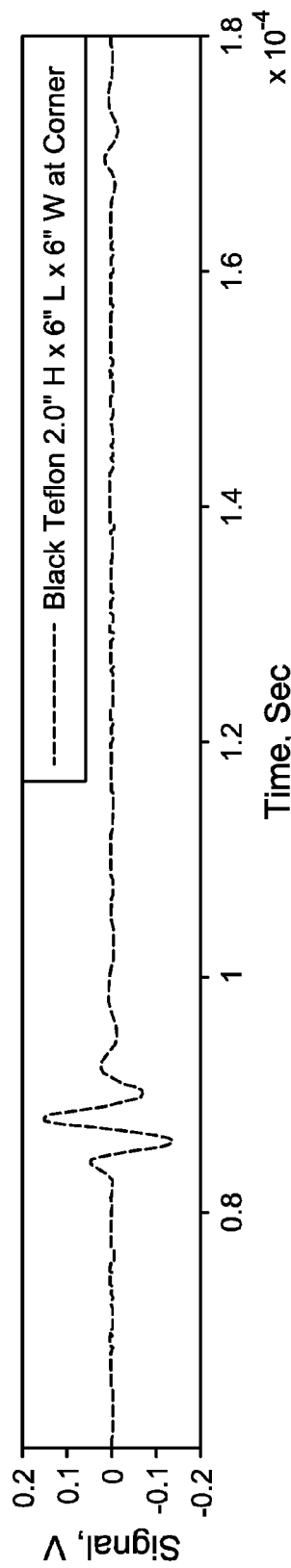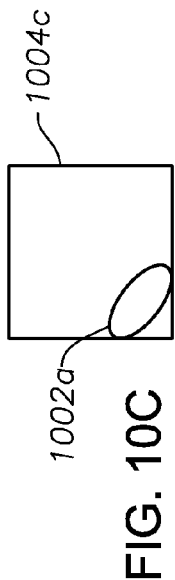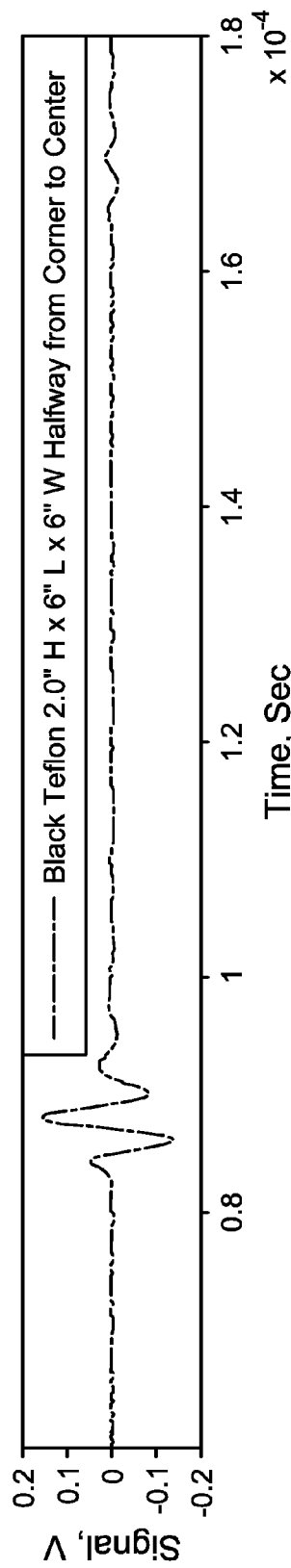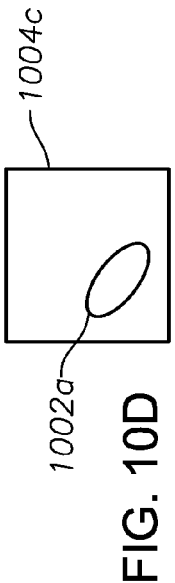

ACOUSTIC INTERFACE DEVICE

CROSS-REFERENCE TO RELATED APPLICATIONS

Not applicable.

STATEMENT REGARDING FEDERALLY SPONSORED RESEARCH

Not applicable.

TECHNICAL FIELD OF THE INVENTION

The present disclosure relates generally to systems, methods, and apparatuses using ultrasonic signals for measurement, testing or the like, and more particularly, to an acoustic interface device for use with the same.

BACKGROUND

Ultrasonic techniques are commonly used for non-destructive testing or evaluation (NDT or NDE) of materials, e.g., by measurement of properties of the material such as ultrasonic velocity and attenuation. One area in which such ultrasonic techniques are applied is the evaluation of underground/undersea geological formations for determining the presence or absence of hydrocarbons (e.g., petroleum and natural gas) and the evaluation of the quality of casing and cement used in boreholes drilled in such underground/undersea geological formations for discovering and extracting such hydrocarbons.

In such ultrasonic techniques, transducers are commonly used to transmit acoustic signals into the specimen of interest (material under test) and to receive responses to the transmitted signals, e.g., reflections or echoes thereof, the characteristics of which are analyzed to yield information about the properties of material under test. Under certain adverse conditions, e.g., under high temperature or pressure, in a corrosive environment, or when the specimen is very small, it is not feasible to use a transducer in direct contact with the specimen. Such adverse conditions may obtain in the underground/undersea exploration for hydrocarbons described above.

One conventional way of mitigating or overcoming such adverse conditions is by using a buffer rod between the transducer and the specimen. The buffer rod eliminates direct contact between the transducer and the specimen and thus protects the transducer from the adverse conditions present in the specimen environment. When acoustic properties of the buffer rod are known, these known properties in combination with the acoustic response can help in determining acoustic properties of the specimen. However, buffer rods suffer from the problem of spurious (trailing) echoes that interfere with the signal of interest (the response signal described above) received by the transducer. As these spurious echoes are caused at least in significant part by mode conversion at the buffer rod boundaries, they have been mitigated or overcome by making the buffer rod large, tapered, or grooved. However, such buffer rods are too large for accommodation in a downhole tool (e.g., a wireline or logging while drilling (LWD) tool) such as is used in boreholes for exploring for hydrocarbons underground/undersea.

Accordingly, there is a need for improving the accuracy and sensitivity of ultrasonic techniques for evaluation of materials, such as with use of a buffer rod, where the techniques can be performed and the equipment required therefor can be accommodated in a downhole tool.

SUMMARY

Systems, apparatuses and methods that use an acoustic interface device are provided. These systems, apparatuses and methods may improve the accuracy and sensitivity of ultrasonic measurement techniques that may be employed, inter alia, in a downhole environment.

According to a first aspect of the invention, there is provided a system including an acoustic interface device, configured for coupling to a transducer and to a specimen. The acoustic interface device has a material composition having a shear wave attenuation coefficient $\alpha_S$ of at least about 5 dB/cm when subjected to an acoustic signal at a frequency between about 200 to 500 kHz.

According to a second aspect of the invention, there is provided a system including an acoustic interface device, configured for coupling to a transducer and to a specimen. The acoustic interface device is formed from a material from the group consisting of: polytetrafluoroethylene (Teflon®), a perfluoroalkoxy alkane (PFA), polycarbonate (Lexan®), and polyether ether ketone (PEEK).

According to a third aspect of the invention, there is provided a process including the following operations: providing an acoustic interface device, coupled to a transducer; coupling the acoustic interface device to a specimen; by the transducer, generating a first acoustic signal, such that the generated first acoustic signal is transmitted to the acoustic interface device; and receiving a second acoustic signal in response to the transmitted first acoustic signal. The acoustic interface device has a material composition having a shear wave attenuation coefficient $\alpha_S$ of at least about 5 dB/cm when subjected to an acoustic signal at a frequency between about 200 to 500 kHz.

According to a fourth aspect of the invention, there is provided a process including the following operations: providing an acoustic interface device, coupled to a transducer; coupling the acoustic interface device to a specimen; by the transducer, generating a first acoustic signal, such that the generated first acoustic signal is transmitted to the acoustic interface device; and receiving a second acoustic signal in response to the transmitted first acoustic signal. The acoustic interface device is formed from a material from the group consisting of: polytetrafluoroethylene (Teflon®), a perfluoroalkoxy alkane (PFA), polycarbonate (Lexan®), and polyether ether ketone (PEEK).

BRIEF DESCRIPTION OF THE DRAWINGS

The following figures form part of the present specification and are included to further demonstrate certain aspects of the present claimed subject matter, and should not be used to limit or define the present claimed subject matter. The present claimed subject matter may be better understood by reference to one or more of these drawings in combination with the description of embodiments presented herein. Consequently, a more complete understanding of the present embodiments and further features and advantages thereof may be acquired by referring to the following description taken in conjunction with the accompanying drawings, in which like reference numerals may identify like elements, wherein:

FIG. 3 illustrates a measurement cell for ultrasonic testing of a fluid, suitable for use in a logging while drilling (LWD) tool, according to some embodiments;

FIG. 4 illustrates an LWD tool containing the measurement cell of FIG. 3, according to some embodiments;

FIG. 8 illustrates four graphs, each graph being of a respective acoustic waveform (signal amplitude versus time) showing reflections of an acoustic signal transmitted into a respective buffer rod, where each buffer rod has a respective one of four different material compositions;

FIGS. 10A-10D illustrate respectively four different spatial arrangements of a transducer and an acoustic interface device, and FIGS. 10E-H illustrate respective graphs showing acoustic waveforms (signal amplitude versus time) of pulse-echo responses corresponding to the arrangements of FIGS. 10A-D, respectively, according to some embodiments;

NOTATION AND NOMENCLATURE

Figure 1:
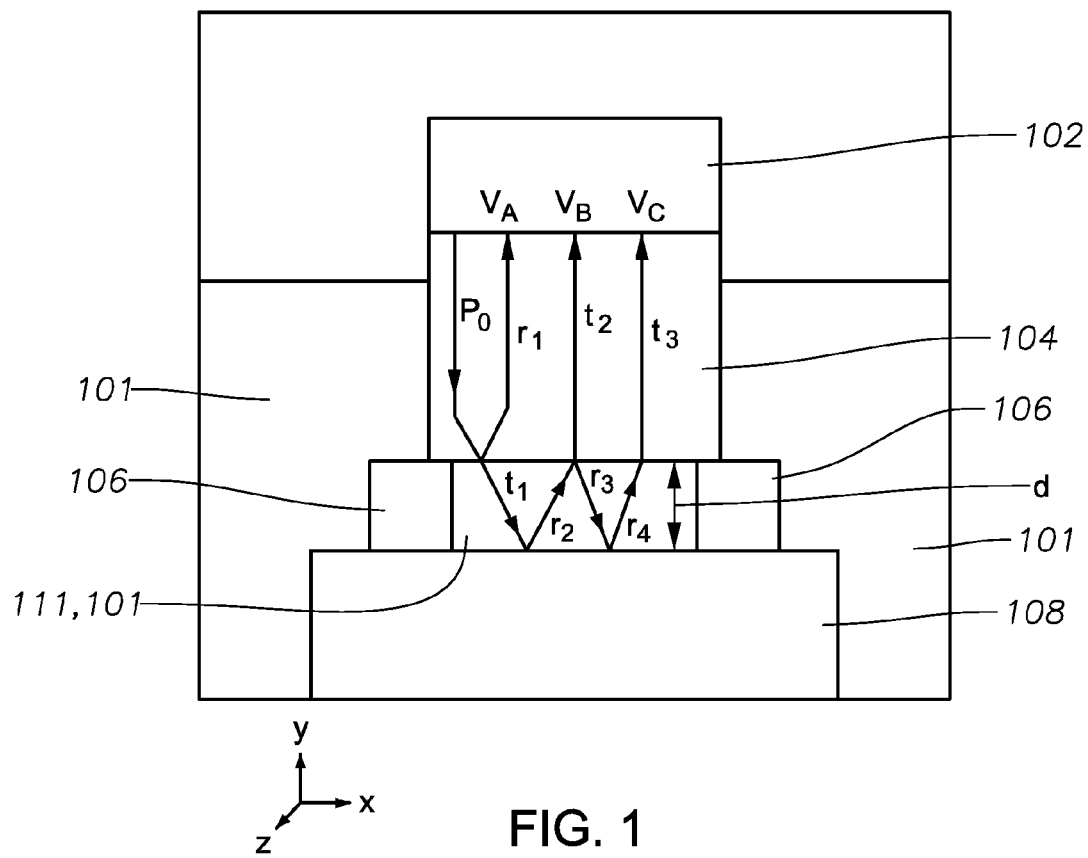
FIG. 1 illustrates a measurement cell for ultrasonic testing of a fluid, according to some embodiments.

Certain terms are used throughout the following description and claims to refer to particular system components and configurations. As one skilled in the art will appreciate, the same component may be referred to by different names. This document does not intend to distinguish between components that differ in name but not function. In the following discussion and in the claims, the terms "including" (and the like) and "comprising" (and the like) are used in an open-ended fashion, and thus should be interpreted to mean "including, but not limited to . . . ."

The term "couple" and cognate terms as used herein in the context of ultrasonic testing are to be construed broadly as encompassing any kind of coupling, including, as non-limiting examples, (i) coupling involving the use of a coupling medium (which could be air or another medium, e.g., an oil or gel) between the elements to be coupled, (ii) coupling by bonding together the elements to be coupled, e.g., using an adhesive, and (iii) coupling by disposing the elements to be coupled in direct contact with each other, without the use of any coupling medium.

DETAILED DESCRIPTION

The foregoing description of the figures is provided for the convenience of the reader. It should be understood, however, that the embodiments presented herein are not limited to the precise arrangements and configurations shown in the figures. Also, the figures are not necessarily drawn to scale, and certain features may be shown exaggerated in scale or in generalized or schematic form, in the interest of clarity and conciseness. Relatedly, certain features may be omitted in certain figures, and this may not be explicitly noted in all cases.

While various embodiments are described herein, it should be appreciated that the present invention encompasses many inventive concepts that may be embodied in a wide variety of contexts. The following detailed description of exemplary embodiments, read in conjunction with the accompanying drawings, is merely illustrative and is not to be taken as limiting the scope of the invention, as it would be impossible or impractical to include all of the possible embodiments and contexts of the invention in this disclosure. Upon reading this disclosure, many alternative embodiments of the present invention will be apparent to persons of ordinary skill in the art. The scope of the invention is defined by the appended claims and equivalents thereof.

Illustrative embodiments of the invention are described below. In the interest of clarity, not all features of an actual implementation are described or illustrated in this specification. In the development of any such actual embodiment, numerous implementation-specific decisions may need to be made to achieve the design-specific goals, which may vary from one implementation to another. It will be appreciated that such a development effort, while possibly complex and time-consuming, would nevertheless be a routine undertaking for persons of ordinary skill in the art having the benefit of this disclosure.

In the following, a description is given of acoustic interface devices, and of measurement cells in which acoustic interface devices may be used, for ultrasonic testing, according to some embodiments. The organization of the following description is generally to set forth first the structure of the components and systems, and thereafter the operation and use thereof. Thus, the structure may be presented initially in a manner that omits details of the context of operation and use, and the subsequent description of operation and use may serve to clarify and contextualize aspects of the structure.

FIG. 1 is a schematic illustration of a measurement (or test) cell (or chamber) 100 for ultrasonic testing of a specimen or material under test, which may be a fluid 101, according to some embodiments. In addition to holding fluid 101, measurement cell 100 includes a transducer 102, which may be a piezoelectric transducer. Examples of such a transducer include the following: a 250 kHz 70% bandwidth piezo-composite transducer (circular, rectangular or oval shaped); and a 500 kHz wideband 1" diameter transducer, such as the immersion type V301 by Olympus. More generally, transducer 102 may be a transducer that is operable to generate acoustic signals at least at a frequency between about 200 to 500 kHz in response to an applied electric voltage.

Measurement cell 100 further includes an acoustic interface device 104. Acoustic interface device 104 may have the shape of a cylinder, square plate, or another shape. As shown, acoustic interface device 104 may interface at a proximal end thereof (upper end in FIG. 1) with transducer 102 and may function, e.g., as a buffer rod, noise dampener and/or delay line. Further description of the structure and operation of acoustic interface device 104 will be provided below, in part with reference to FIG. 2. The interface (coupling) between transducer 102 and acoustic interface device 104 may be achieved in any suitable manner, as will be understood by one of ordinary skill in the art. For example, this interface may be achieved by coupling using a coupling medium, e.g., an oil, a gel, an epoxy, etc. As another example, this interface or coupling may be achieved by bonding the transducer to the acoustic interface device using, e.g., an epoxy bond.

Measurement cell 100 further includes a spacer 106 and a reflector 108. Reflector 108 may be a stainless steel plate (having an impedance of approximately 45 MRayls), or it may be made of another suitable material that has an acoustic impedance significantly higher than that of the fluid being tested (which is typically 1.5 to 3 MRayls), for example, corrosion resistant metals such as titanium (25 MRayls) or Inconel® (55 MRayls) or even a tungsten loaded epoxy (9.5 MRayls for 25% tungsten by volume in EPO-TEK 301®). The stainless steel reflector is preferably at least 4.0 inch in thickness to reduce ringing and to delay reflections in the steel, which reflections might interfere with the signal of interest.

Spacer 106 may include multiple component spacers, as illustrated in FIG. 1. For convenience, spacer 106 may be referred to herein in either the singular or the plural, it being understood that the singular may refer collectively to multiple component spacers. As shown, spacer 106 may interface with acoustic interface device 104 at a proximal end of spacer 106 (upper end in FIG. 1) and a distal end of acoustic interface device 104 (lower end in FIG. 1). Further, as shown, spacer 106 may interface with acoustic interface device 104 over only a portion of the distal end of acoustic interface device 104, e.g., at peripheral regions of acoustic interface device 104 (lower end in FIG. 1). As further shown, spacer 106 may interface with reflector 108 at a distal end of spacer 106 (lower end in FIG. 1) and a proximal end of reflector 108 (upper end in FIG. 1). In the arrangement described, spacer 106 may be attached to acoustic interface device 104 and to reflector 108 by suitable means known to one of ordinary skill in the art.

In the arrangement described, as illustrated, spacer 106 provides for a fluid gap 111 between (distal end of) acoustic interface device 104 and (proximal end of) reflector 108, in which fluid 101 freely flows to fill fluid gap 111. (FIG. 1 may be understood to be a cross-section taken in the y-direction. The region identified as fluid gap 111 is in fluid communication with the regions at the right and left sides of measurement cell 100 identified as containing fluid 101, but this fluid communication between these regions is not visible due to the two-dimensional nature of the figure. In this regard, if the setup shown in the figure were construed as two-dimensional it would appear as if spacers 106 form a physical barrier between fluid gap 111 and the regions at the right and left sides of measurement cell 100 identified as containing fluid 101, which barrier would prevent fluid communication therebetween.) The extent of fluid gap 111 in the y-direction is d. Spacer 106 maintains this fixed distance d between (distal end of) acoustic interface device 104 and (proximal end of) reflector 108.

Acoustic interface device 104 may be partly immersed in fluid 101 in fluid gap 111. As a non-limiting example, about half of the height of acoustic interface device 104 may be immersed, although FIG. 1 shows that the level of fluid 101 reaches higher than the midpoint of the height of acoustic interface device 104. (The height of acoustic interface device 104 refers to its extent in the y-direction in FIG. 1, in other words, the distance from its distal end at spacer 106 to its proximal end at transducer 102. In a context other than that of FIG. 1, what is referred to here as the height of acoustic interface device 104 may be referred to as its length.)

Reflector 108 serves to reflect acoustic waves that have been transmitted from transducer 102 and have traveled through acoustic interface device 104 and fluid 101 in fluid gap 111 (or that have been reflected at the interface of acoustic interface device 104 and fluid 101 in fluid gap 111). Acoustic waves reaching reflector 108 are reflected back through fluid 101 in fluid gap 111 in the direction of acoustic interface device 104 (upward in FIG. 1), and some of these acoustic waves travel through acoustic interface device 104 and reach transducer 102. The behavior of the acoustic waves is described in further detail below in the context of the operation and use of measurement cell 100.

Figure 2:
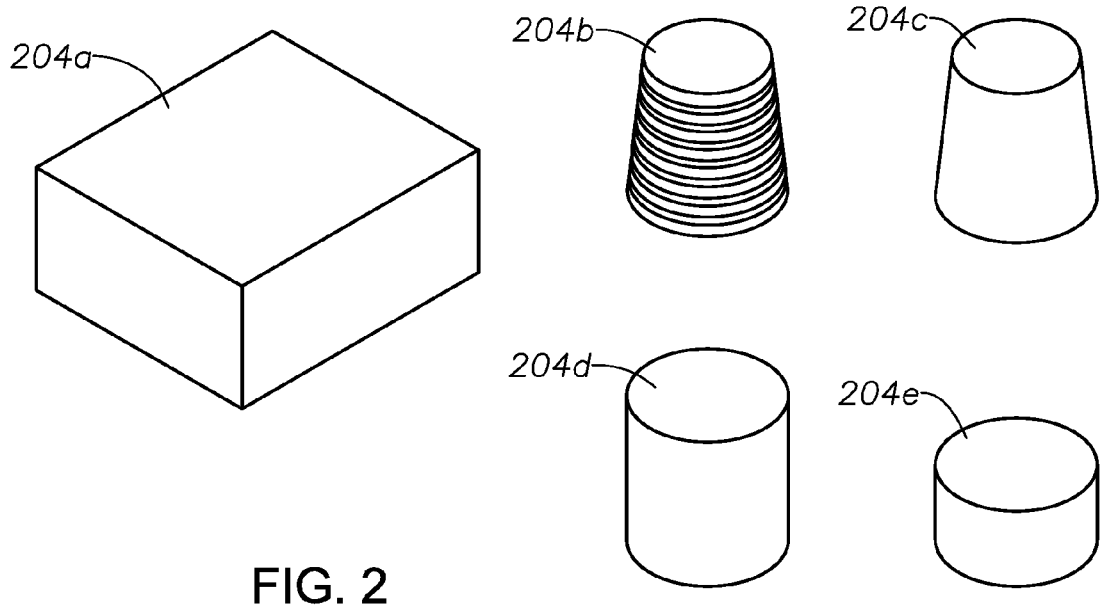
FIG. 2 illustrates acoustic interface devices of different sizes and shapes, which may be used in a measurement cell, according to some embodiments.

Dimensions of components and aspects of the arrangement described above may be as follows. Transducer 102 may have an oval shape with a length of 1.65 inches, a width of 0.75 inches and a thickness (height in FIG. 1) of 1.25 inches. Alternatively, transducer 102 may be a typical one inch diameter transducer, with a thickness (height in FIG. 1) of, e.g., 1.25 inches. Acoustic interface device 104 may have dimensions similar to these dimensions of transducer 102. Some exemplary configurations (size and shape) of acoustic interface device 104 are seen in FIG. 2, which illustrates acoustic interface devices of different sizes and shapes, which may be used in a measurement cell, according to some embodiments. As seen in FIG. 2: an acoustic interface device 204a is a square plate of the following dimensions: 6.0 inches in length, 6.0 inches in width, and 2.0 inches in thickness (height); an acoustic interface device 204b is a tapered, grooved cylinder of the following dimensions: 1.75 inches in minimum outer diameter, 2.125 inches in maximum outer diameter, and 2.0 inches in height (the tapered, grooved cylinder has ten grooves with a slot width of 0.094 inches and slot depth of 0.063 inches); an acoustic interface device 204c is a tapered cylinder of the following dimensions: 1.75 inches in minimum outer diameter, 2.125 inches in maximum outer diameter, and 2.0 inches in height; an acoustic interface device 204d is a cylinder of the following dimensions: 1.75 inches in diameter and 1.75 inches in height; and an acoustic interface device 204e is a cylinder of the following dimensions: 1.625 inches in diameter and 1.25 inches in height. Other exemplary configurations of acoustic interface device 104 not shown in FIG. 2 are cylinders of the following dimensions: 1.75 inches in diameter and 2.0 inches in height; 2.0 inches in diameter and 2.0 inches in height; 3.125 inches in diameter and 2.0 inches in height. Other shapes and sizes of acoustic interface device 104 may also be employed. Turning back to FIG. 1, exemplary dimensions of reflector 108 are: a diameter of 2.0 inches and a height of preferably 4.0 inches or more. With regard to fluid gap 111, the distance d (extending in the y-direction in FIG. 1) may be, e.g., 10 mm, 19 mm, 20 mm, or another magnitude. As will be appreciated by one of skill in the art, dimensions other than those set forth herein may be employed. Accordingly, the dimensions given herein are merely exemplary in nature and should not be taken as so limiting the invention. Also, dimensions listed above may be approximations.

As will be understood, not all aspects of measurement cell 100 are necessarily shown in FIG. 1. One of ordinary skill in the art will understand that certain additions, substitutions and variations may be made.

Figure 5:
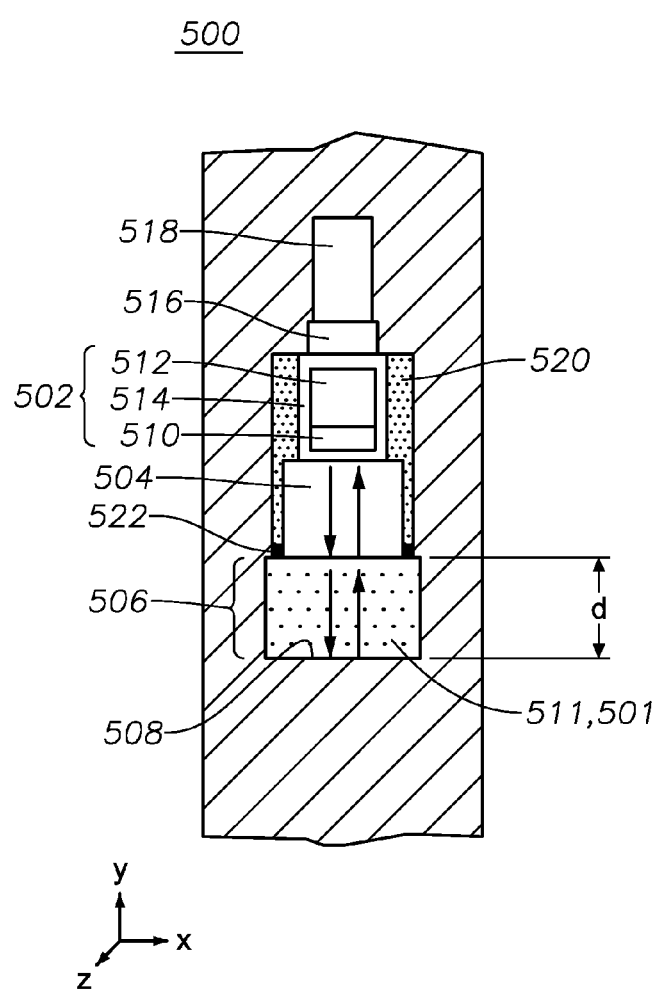
FIG. 5 illustrates a measurement cell for ultrasonic testing of a fluid, suitable for use in a wireline tool, according to some embodiments.

Measurement cell 100 may be thought of as a generalized measurement cell 100 that may be used in or, if necessary, adapted to, any suitable context or environment. FIGS. 3 and 5 illustrate variants of measurement cell 100 for use in downhole tools. Measurement cell 100 or variants thereof may also be used in uphole environments. Generally, the description of measurement cell 100 (including components thereof) given above applies also to the measurement cells of FIGS. 3 and 5 described below, unless indicated otherwise, whether explicitly or by logical implication of the description as a whole in light of the knowledge of one of ordinary skill in the art. Accordingly, for convenience, not all aspects of measurement cell 100 that apply to the measurement cells of FIGS. 3 and 5 are necessarily repeated in the description of the latter. It is noted, however, that the measurement cells of FIGS. 3 and 5 are in some respects described in greater detail than is measurement cell 100, and such detail is generally applicable to measurement cell 100 unless indicated otherwise, whether explicitly or by logical implication of the description as a whole in light of the knowledge of one of ordinary skill in the art.

It is noted that measurement cell 100 and the measurement cells of FIGS. 3 and 5, including the components of these cells, may be designed to be operable under at least the following conditions: between temperatures of about 150 and 200 degrees Celsius, inclusive; and at pressures between about 20,000 and 35,000 psi, inclusive.

FIG. 3 is a schematic illustration of a measurement cell 300 (enlarged view) for use in a logging while drilling (LWD) tool, while FIG. 4 is a schematic illustration of a portion of an LWD tool in a borehole, the tool containing measurement cell 300 (reduced, inset view). FIG. 4 illustrates a cross-section taken in the vertical or axial direction of the generally cylindrical borehole and tool. Accordingly, the structures shown in FIG. 4 exhibit a left-right symmetry about the hollow center of the tool, except for measurement cell 300, which is located on one side of the tool. With reference to FIG. 4, LWD collar (drill collar) 490 extends downward in a borehole, which has been bored in formation 491. The portion of the borehole surrounding LWD collar 490 is referred to as a borehole annulus 493. Mud (drilling fluid) flows into the hollow center of the LWD tool, downward, at arrow 495, and returns, upward, to the surface, in borehole annulus 493 at arrows 497. A portion of the collar 490 is gouged out to accommodate measurement cell 300. For convenience, the elements of measurement cell 300 are identified only in FIG. 3.

Turning to FIG. 3, measurement cell 300 includes transducer 302, acoustic interface device 304 and reflector 308. Acoustic interface device 304 may, but need not, be cylindrical, as depicted. Transducer 302 includes piezoelectric element 310, transducer backing 312, and transducer housing 314 (these transducer components were omitted from FIG. 1 for convenience). A connector 316 and an electronic board 318 are provided for applying electric (voltage) signals to transducer 302 (these components were omitted from FIG. 1 for convenience). In response to an applied voltage, transducer 302 generates acoustic waves. The acoustic waves are transmitted (downward arrows in FIG. 3) through acoustic interface device 304 and fluid 301 in fluid gap 311 and are reflected by reflector 308 (upward arrows in FIG. 3) back through fluid 301 in fluid gap 311 and acoustic interface device 304 to transducer 302. As explained with reference to FIG. 1, not all acoustic waves travel these entire distances; some are reflected at the interface between acoustic interface device 304 and fluid 301 in fluid gap 311. Accordingly, the depiction of the travel of the acoustic waves by the arrows in FIG. 3 is an oversimplification and does not purport to show the full complexity thereof. The representation of the travel of the acoustic waves given by the arrows in FIG. 1 is applicable to measurement cell 300 and is more accurate. The behavior of the acoustic waves will be described below in the context of the operation and use of the measurement cells.

As seen in FIG. 3, fluid 301, which in this case is mud 497, flows freely between borehole annulus 493 and fluid gap 311. As measurement cell 300 is accommodated in a hollowed out portion of LWD collar 490, a portion 306 of LWD collar 490 serves as a spacer in this arrangement, such that a fixed distance d is maintained between acoustic interface device 304 and reflector 308. (This portion 306 may be referred to as spacer 306.) Other structures or arrangements for spacer 306 may be employed. Also, of note, as measurement cell 300 is accommodated in a hollowed out portion of LWD collar 490, in the case in which LWD collar 490 is made of stainless steel or another suitable material, the surface of LWD collar 490 itself that is facing fluid gap 311 may serve as reflector 308. Again, other structures or arrangements for reflector 308 may be employed.

As further illustrated in FIG. 3, an oil fill 320 is provided surrounding transducer 302 and acoustic interface device 304, and a sealing ring (o-ring) 322 is provided around the distal end of acoustic interface device 304 (i.e., where acoustic interface device 304 interfaces with fluid 301 at fluid gap 311), to prevent entry of fluid 301 into transducer 302 and acoustic interface device 304, because such entry of fluid 301 could contaminate and damage those components. (Oil fill 320 and sealing ring (o-ring) 322 may be included in the arrangement of FIG. 1, but are omitted in that figure for convenience.)

Figure 6:
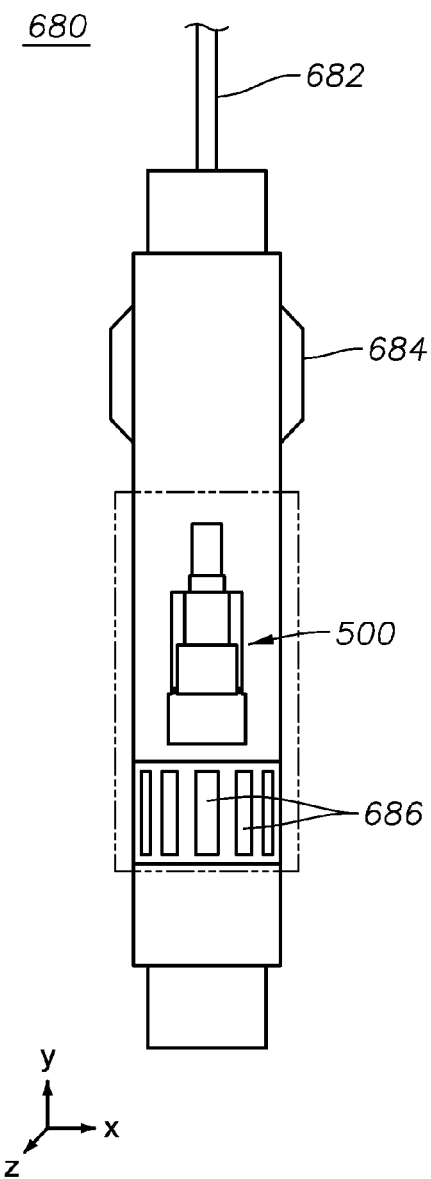
FIG. 6 illustrates a wireline tool containing the measurement cell of FIG. 5, according to some embodiments.

FIG. 5 is a schematic illustration of a measurement cell 500 (enlarged view) for use in a wireline tool (and shown in a portion of such wireline tool), while FIG. 6 is a schematic illustration of a wireline tool for use in a borehole, the tool containing measurement cell 500 (reduced, inset view). As with FIG. 4, so too FIG. 5 illustrates a cross-section taken in the vertical or axial direction of the generally cylindrical wireline tool.

With reference to FIG. 6, wireline tool 680 includes a cable 682 and a centralizer 684 for use in lowering wireline tool 680 into and raising wireline tool 680 out of a borehole (not shown), which has been bored in a formation (not shown). Measurement cell 500 is accommodated in a hollow portion of wireline tool 680. Wireline tool 680 is provided with a mud flow window 686. Mud flow window 686 may have a cage-like structure, and may be vertically centered at or near the level of fluid gap 511 (FIG. 5) when measurement cell 500 is seated in wireline tool 680, such that mud may freely flow between the borehole and fluid gap 511.

With reference to FIG. 5, measurement cell 500 may include a structure and arrangement of parts similar or identical to that of measurement cell 300 as described above, namely including, e.g., transducer 502, which includes piezoelectric element 510, transducer backing 512, and transducer housing 514; connector 516; electronic board 518; acoustic interface device 504; oil fill 520; sealing ring 522; spacer 506; reflector 508; and fluid gap 511. Through mud flow window 686, fluid 501, which in this case is mud, may flow freely into fluid gap 511 from the borehole and from fluid gap 511 into the borehole. As with measurement cell 300 in the LWD tool, so too in the case of measurement cell 500 in wireline tool 680, applicable portions of the tool itself may, but need not, serve as spacer 506 and reflector 508, respectively. In view of the correspondence of components (and their functions) between measurement cell 500 and measurement cell 300, the description of measurement cell 300 given above is understood to apply generally to measurement cell 500.

Further description will now be given of acoustic interface devices 104, 304, 504, a non-exhaustive set of example configurations (sizes and shapes) of which are illustrated in and described with reference to FIG. 2. As this description applies to any and all of acoustic interface devices 104, 304 and 504, reference will be made to an acoustic interface device generally, without mention of specific reference numbers. The material composition of the acoustic interface device may be one of the following: polytetrafluoroethylene (Teflon®), a perfluoroalkoxy alkane (PFA), polycarbonate (Lexan®), and polyether ether ketone (PEEK). The higher operating temperature polymers are preferred for downhole use. Alternatively, the material composition may be a composite, which includes one or more of the preceding materials and one or more additional materials. Such a composite could be a matrix of a first material that is loaded with a second material. The matrix material may be continuous, while the loaded material may be discontinuous, dispersed within the matrix. The loaded material may but need not be in the form of particles. Examples of such composite material compositions of the acoustic interface device are: (i) carbon-filled Teflon® (Teflon® matrix loaded with carbon particles), and (ii) stainless steel filled Teflon® (e.g., about 20% stainless steel by volume). Other particle-filled composites may also be employed; for example, Teflon® filled with carbon, steel or bronze; or PEEK (or Torlon®) filled with Teflon.

More generally, the material composition of the acoustic interface device may be one having a shear attenuation coefficient $\alpha_S$ of at least about 5 dB/cm when subjected to an acoustic signal at a frequency between about 200 to 500 kHz (i.e., at least at some frequency within this range, not necessarily at every frequency within this range). Further, the material composition of the acoustic interface device may be one having a compressional wave velocity $V_P$ of at most about 1600 m/s at a temperature between about 150 and 200 degrees Celsius and a pressure between about 20,000 to 35,000 psi (i.e., at least at some temperature, not necessarily at every temperature, within this range, and at least at some pressure, not necessarily at every pressure, within this range). Further, the material composition of the acoustic interface device may be one having a shear wave velocity $V_S$ of at most about 1100 m/s at a temperature between about 150 and 200 degrees Celsius and a pressure between about 20,000 to 35,000 psi (i.e., at least at some temperature, not necessarily at every temperature, within this range, and at least at some pressure, not necessarily at every pressure, within this range). Further, the material composition of the acoustic interface device may be one having a compressional wave attenuation coefficient $\alpha_C$ of at most about 6 dB/cm when subjected to an acoustic signal at a frequency between about 200 to 500 kHz (i.e., at least at some frequency, not necessarily at every frequency, within this range).

It will be noted that Teflon® was tested under certain conditions and reported to have a shear attenuation coefficient $\alpha_S$ of 23.2171 dB/cm at 1 MHz, which, assuming a linear variation with frequency, is approximately 5.8 db/cm at 250 kHz, which is significantly higher than that of many other engineering materials, and a shear velocity $V_S$ of 441 m/s, which is significantly lower than that of many other engineering materials. See M. V. M. S. Rao and K. J. Prasanna Lakshmi, "Shear-wave propagation in rocks and other lossy media: An experimental study," *Current Science*, Vol. 8, No. 25, Oct. 25, 2003, page 1224. In addition, the instant inventors have tested Teflon® and PFA found them to have a compressional (p-wave) velocity $V_P$ of approximately 1100-1300 m/s, which is lower than that of many other engineering materials, and a compressional wave attenuation coefficient $\alpha_C$ of 1.0-2.3 dB/cm over 150-400 kHz, which is low to moderate relative to other engineering materials. The significance of these properties is discussed below.

The acoustic interface device may serve any of several different functions. One function of the acoustic interface device is that of a buffer rod, that is, to provide a buffer between the transducer and the specimen of interest or material under test. Such a buffer may be useful or necessary, for example, where the conditions of the specimen (or specimen environment) are such as could damage the transducer, e.g., high temperature or pressure, or corrosive liquid. A buffer rod may also be useful or needed in the case of a small sample size, in order to obtain good contact with the specimen of interest. The acoustic interface device may also serve the functions of signal conditioning and noise damping. The acoustic interface device may also serve as a delay line. With shear waves significantly suppressed (due to the above-noted relatively high shear wave attenuation), an acoustic interface device formed of a material having a preferred (low, as noted above) compressional velocity provides a longer time window for receipt/capture of the response signal, since the compressional wave signal returns from the specimen without much interference from the second reflection from the interface of the specimen and the acoustic interface device. (This "second reflection" is explained as follows: in FIG. 1, when $r_1$ arrives at transducer 102 at $V_A$, a portion of $r_1$ (not shown) is reflected back in acoustic interface device 104, downward in FIG. 1, toward fluid gap 111. When this portion of $r_1$ reaches the interface between acoustic interface device 104 and fluid gap 111, a part of this portion of $r_1$ is reflected, upward in FIG. 1, back toward transducer 102 and arrives at transducer 102. This portion that arrives at transducer 102 is the "second reflection.")

One problem with prior art buffer rods is that the acoustic signal generated by the transducer and transmitted through the rod, which is a compressional acoustic wave (p-wave), may strike the circumferential edge of the rod and generate shear waves due to mode conversion at the boundary. These shear waves may overlap in time with the signal of interest (i.e., the reflection of the transmitted signal, explained below) that is to be received by the transducer and measured. These shear waves thus constitute spurious (or trailing) echoes, in effect, noise, that degrade the signal of interest or the ability to capture and interpret it (e.g., the signal-to-noise ratio). Thus, these spurious echoes diminish the accuracy with which acoustic properties of the specimen can be measured, and hence the quality of the information that can be obtained about the physical properties of the specimen/ specimen environment (e.g., borehole casing/cement) under investigation. As noted, prior art efforts to mitigate this problem have included using a large buffer rod for noise delay, and using a tapered and/or grooved buffer rod to reduce generation of mode converted waves. However, these prior art mitigations are generally not suitable for use in a downhole tool, as, for example, the size of the buffer rod may not be accommodated in the tool, due to the limited space inside the tool.

By virtue of using materials such as the specific materials and compositions described above, or materials satisfying properties described above, however, an acoustic interface device, which can serve as a buffer rod, may be fashioned that is sufficiently small to be accommodated in a downhole tool (e.g., of a diameter and length (i.e., height in FIGS. 1 and 3-6) similar to that of a transducer), and that significantly reduces noise, e.g., spurious echoes and ringing noise. With such an acoustic interface device, a much cleaner signal of interest can be obtained, supporting enhanced signal sensitivity and accuracy of measurement, so as to yield more accurate and reliable information of acoustic properties and associated physical features. The improvements in the determination of acoustic properties of a specimen and such associated information will be more fully understood in light of the following discussion of the operation and use of the measurement cells described herein.

Figure 7:
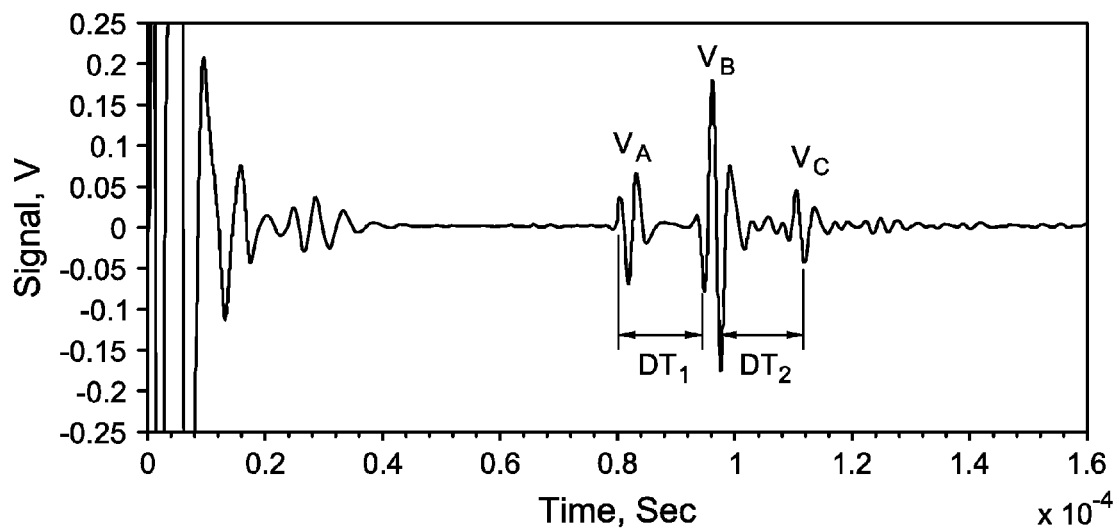
FIG. 7 illustrates a graph of an acoustic waveform (signal amplitude versus time) showing reflections of an acoustic signal that was transmitted into a specimen via an acoustic interface device, according to some embodiments.

Operation and use of measurement cells 100, 300 and 500 will be discussed with reference to FIG. 7. Again, as this discussion applies to any and all of measurement cells 100, 300 and 500, reference will be made to a measurement cell generally, without mention of specific reference numbers. FIG. 7 illustrates a graph of an acoustic waveform showing reflections of an acoustic signal that was transmitted into a specimen via an acoustic interface device, according to some embodiments. On the graph, the y-axis indicates signal amplitude and the x-axis indicates time. A measurement cell such as described herein may be used to measure/determine acoustic properties of a specimen or material (e.g., a fluid) under test, e.g., the properties of acoustic impedance, sound velocity, and attenuation. In the context of (cemented, cased) boreholes, these properties may be used to obtain a cement bond log (CBL), which may provide information regarding the thickness of the casing, how well the cement is adhering to the casing, and the quality and acoustic impedance of the cement behind the casing.

As will be understood from the arrangements of the measurement cells described herein, these cells may be used to conduct pulse-echo measurements. In a pulse-echo measurement, a pulse (acoustic signal) is transmitted by the transducer, and reflections (echoes) of the transmitted pulse are received by the transducer and measured. (In this regard, it is noted that it is possible for a measurement cell described herein to employ two separate transducers, one for transmitting acoustic signals and one for receiving reflections thereof. For example, the transducer+acoustic-interface-device portion of the above-described arrangements could be replaced by a transmitting-transducer+first-acoustic-interface-device+receiving-transducer+second-acoustic-interface-device portion.)

Using pulse-echo measurements, one method that can be used to obtain acoustic properties of the specimen is the multiple reflection method (MRM), also known as the ABC method, which was devised by E. P. Papadakis ("Buffer-Rod System for Ultrasonic Attenuation Measurements," *J. Acoust. Soc. Am.* 44, 1437-1441, 1968). With reference to FIGS. 1 and 7, initially a pulse $P_0$ (acoustic signal) is generated by transducer 102 and transmitted through acoustic interface device 104 in the direction of the fluid 101 in fluid gap 111, which is also the direction of the reflector 108. When pulse $P_0$ arrives at the interface of acoustic interface device 104 and the fluid 101 in fluid gap 110, due to the difference in acoustic impedance between acoustic interface device 104 and fluid 101 in fluid gap 111, a portion $t_1$ of the signal $P_0$ is transmitted through fluid 101, continuing in the direction of reflector 108, and a portion $r_1$ of the signal $P_0$ is reflected back in the direction of acoustic interface device 104, returning in the direction of transducer 102, according to the well-known equations for acoustic transmission and reflection at a boundary between materials of different acoustic impedances, which for normal incidence, gives the fraction of reflected acoustic energy as $[(Z_1-Z_2)/(Z_1+Z_2)]^2$ and the corresponding fraction of transmitted energy as one minus the fraction of energy reflected when assuming no energy loss at the interface. The portion $r_1$ returns to and is received by transducer 102, indicated as $V_A$ in FIG. 1 and as peak $V_A$ in FIG. 7. The portion $t_1$ reaches reflector 108 and is reflected back (for clarity relabeled as portion $r_2$) in the direction of acoustic interface device 104, which is also the direction of transducer 102. (In practice, reflector 108 will not reflect 100% of portion $t_1$; some of portion $t_1$ may be transmitted through reflector 108 or dissipated.) When portion $r_2$ reaches the interface of acoustic interface device 104 and the fluid 101 in fluid gap 110, a portion of $r_2$ is transmitted through acoustic interface device 104 (as portion $t_2$), continuing in the direction of transducer 102, and a portion of $r_2$ is reflected back (as portion $r_3$) in the direction of reflector 108. The portion $t_2$ returns to and is received by transducer 102, indicated as $V_B$ in FIG. 1 and as peak $V_B$ in FIG. 7. The portion $r_3$ reaches reflector 108 and is reflected back (as portion $r_4$) in the direction of acoustic interface device 104, which is also the direction of transducer 102. (In practice, reflector 108 will not reflect 100% of portion $r_3$; some of portion $r_3$ may be transmitted through reflector 108 or dissipated.)

When portion $r_4$ reaches the interface of acoustic interface device 104 and the fluid 101 in fluid gap 110, a portion of $r_4$ is transmitted through acoustic interface device 104 (as portion $t_3$), continuing in the direction of transducer 102, and a portion of $r_4$ is reflected back (not shown) in the direction of reflector 108. The portion $t_3$ returns to and is received by transducer 102, indicated as $V_C$ in FIG. 1 and as peak $V_C$ in FIG. 7. The processes of reflection and transmission continue until the signal is completely absorbed or dissipated.

The amplitudes, and the arrival times at transducer 102, of peaks $V_A$, $V_B$ and $V_C$ are measured (described below). The reflection coefficient R, which is a measure of how much of the signal is reflected, is obtained using Equation (1):

$$R = \pm (|1-(V_B^2/V_A V_C)|)^{-0.5} \qquad (1)$$

Given R, the acoustic impedance of fluid 101 in fluid gap 111, $Z_f$ is calculated using Equation (2):

$$Z_f = Z_{aid}(1+R)/(1-R) \qquad (2)$$

where $Z_{aid}$ is the acoustic impedance of acoustic interface device 104, which is known.

The sound velocity of fluid 101 in fluid gap 111, c, is calculated as the distance traveled by the acoustic signal ($P_0$ and as subsequently renamed, as described above) divided by the travel time. It can be seen that the acoustic signal travels a distance 2d (FIG. 1) in the time interval DT1 or DT2 (FIG. 7). This may be explained as follows. The acoustic signal arrives at $V_A$ (FIG. 1) at the starting point (left side) of interval DT1 (FIG. 7). The acoustic signal arrives at $V_B$ (FIG. 1) at the end point (right side) of interval DT1 (FIG. 7). The distance traveled by the acoustic signal during the time interval DT1 is 2d, because the distance traveled by the acoustic signal at $V_B$ (FIG. 1) exceeds the distance traveled by the acoustic signal at $V_A$ (FIG. 1) by 2d. This is seen as follows. The distance traveled by the signal from its start (initial transmission of $P_0$) to $V_A$ (FIG. 1)

equals the distance (seen in FIG. 1) represented by the portion labeled $P_0$ plus the distance (seen in FIG. 1) represented by the portion labeled $r_1$. The distance traveled by the signal from its start (initial transmission of $P_0$) to $V_B$ (FIG. 1) equals the distance (seen in FIG. 1) represented by the portion labeled $P_0$ plus the distance (seen in FIG. 1) represented by the portion labeled $t_1$ plus the distance (seen in FIG. 1) represented by the portion labeled $r_2$ plus the distance (seen in FIG. 1) represented by the portion labeled $t_2$. Since the distance (seen in FIG. 1) represented by the portion labeled $t_2$ equals the distance (seen in FIG. 1) represented by the portion labeled $r_1$, the difference between the distance traveled by the signal from its start to $V_B$ (FIG. 1) and the distance traveled by the signal from its start to $V_A$ (FIG. 1) equals the distance (seen in FIG. 1) represented by the portion labeled $t_1$ (which is d) plus the distance (seen in FIG. 1) represented by the portion labeled $r_2$ (which is d), or in other words, 2d. A comparable derivation can be performed to show that the distance traveled by the acoustic signal over the time interval DT2 is 2d, because the distance traveled by the acoustic signal at $V_C$ (FIG. 1) exceeds the distance traveled by the acoustic signal at $V_B$ (FIG. 1) by 2d. Thus, the sound velocity (distance/time) of fluid 101 in fluid gap 111, c, is obtained from Equation (3), (4) or (5). Since DT1 and DT2 are measured time intervals, due to practical limits of the accuracy of measurement, they may differ from one another. To compensate for or mitigate this, the average of the sound velocity in the two intervals DT1 and DT2 may be used, per Equation (5).

$$c=2d/DT1 \qquad (3)$$

$$c=2d/DT2 \qquad (4)$$

$$c=4d/(DT1+DT2) \qquad (5)$$

Given $Z_f$ and c, the density of fluid 101 in fluid gap 111 may be calculated by Equation (6).

$$Z_f=\rho c \qquad (6)$$

where ρ is the density of the fluid 101 in fluid gap 111.

Once the values of the acoustic properties of the fluid 101 are known, and, for example, compared at different times, inferences may be drawn from the values of these properties, or their change over time, as to conditions of interest of a cement bond log (CBL), e.g., information regarding the thickness of the casing, how well the cement is adhering to the casing, and the quality of the cement behind the casing.

The improved quality of acoustic signals of interest obtained using acoustic interface devices such as those described herein is demonstrated in FIGS. 8, 9A-9C and 10A-10H.

FIG. 8 shows four pulse echo responses of a wideband 250-kHz transducer (oval, composite transducer, 1.65" L×0.75" W×1.25" H) attached to four buffer rods, respectively, each formed of a different material. The responses are based on reflections from the rod-air interface at the far end of the rod (the end of the rod that is away from the transducer). The four materials, from top to bottom of the figure, are aluminum (2.0" L×2.75" diameter rod), glass (Corning® ULE, 3.0" L×3.0" diameter rod), epoxy (Duralco® 4460, 1.0" L×3.0" diameter rod), and Teflon® (2.0" L×3.125" diameter rod). As clearly seen, the four waveforms differ greatly in signal quality. The rod of Teflon® material shows the best signal quality and the lowest ringing noises by far, among the four materials tested. Note that beyond the initial noise, which all four waveforms have, the Teflon® material shows, relative to the others, a very flat waveform outside of the signal peaks of interest.

Figure 9A:
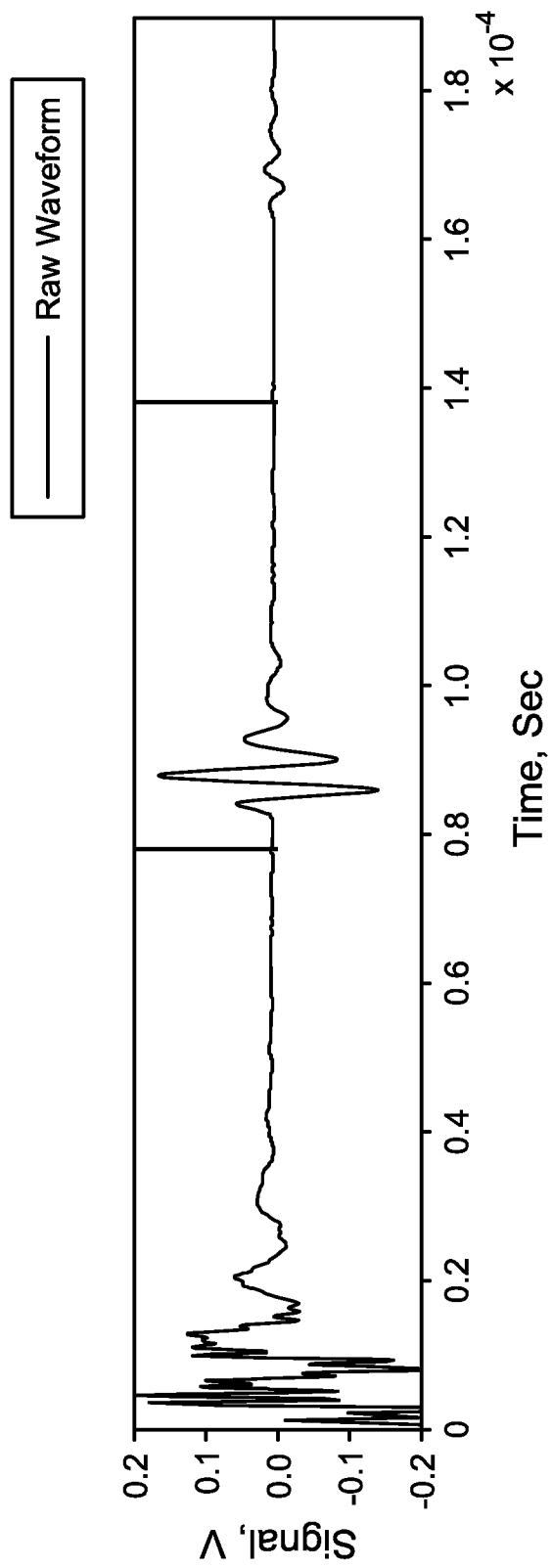
FIG. 9A illustrates a graph showing an acoustic waveform (signal amplitude versus time) showing reflections of an acoustic signal transmitted into an acoustic interface device formed of Teflon®, according to some embodiments.
Figure 9B:
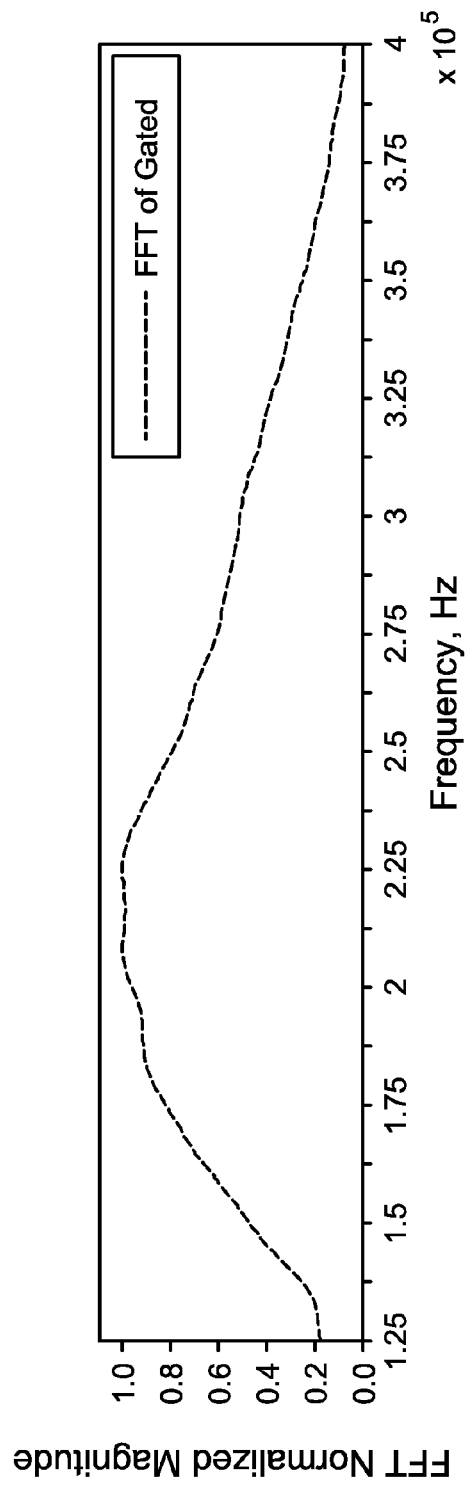
FIG. 9B illustrates a graph showing the Fast Fourier Transform (FFT) spectrum of a portion of the waveform of FIG. 9A, according to some embodiments.
Figure 9C:
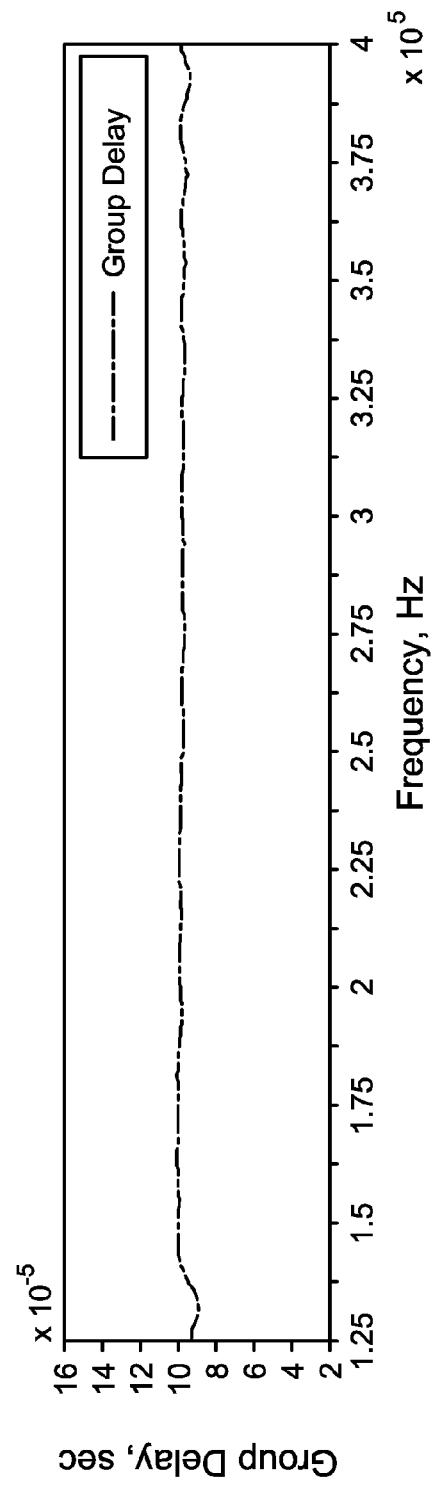
FIG. 9C illustrates a graph showing the group delay spectrum of a portion of the waveform of FIG. 9A, according to some embodiments.

FIGS. 9A-9C shows pulse-echo responses from a wideband 250-kHz transducer (oval, composite transducer, 1.65" L×0.75" W×1.25" H) attached to a Teflon® acoustic interface device (which may serve as a buffer rod) of dimensions 2.0" L×2.0" diameter. Specifically, FIGS. 9A-9C show respectively a raw waveform of the pulse echo response, an FFT spectrum of a portion of the pulse echo response, and a group delay spectrum of a portion of the pulse echo response.

In FIG. 9A, the waveform shows the main echo, which is the reflection from the rear-air interface of the acoustic interface device, at about 90 μs, with a second rear-air interface reflection echo at about 160 μs, and with little noise from about 100 μs to about 160 μs. FIG. 9B shows the FFT spectrum, which has been processed from the windowed signal at 80-140 μs, as indicated by the vertical lines in the graphs of FIGS. 9A and 9B. As seen in FIG. 9B, the FFT spectrum is quite smooth, suggesting few spurious modes or unwanted resonances were present. In FIG. 9C, the group delay (derivative of FFT phase to frequency) spectrum is seen to be very smooth and flat over a wide frequency range of approx. 145-360 kHz, indicating that only few spurious modes or other resonances are present in the Teflon® acoustic interface device and/or the transducer.

FIGS. 10A-10D illustrate respectively four different spatial arrangements of a transducer and an acoustic interface device (cylindrical or square plate), and FIGS. 10E-H illustrate respective graphs showing acoustic waveforms (signal amplitude versus time) of pulse-echo responses corresponding to the arrangements of FIGS. 10A-D, respectively.

For FIGS. 10A-H, the transducer is a 250-kHz oval-shaped wideband transducer. The pulse-echo responses are obtained as follows. The transducer transmits an acoustic signal through the acoustic interface device and receives a response signal (reflection of the transmitted acoustic signal) from the rear end of the acoustic interface device, that is, the interface of the acoustic interface device and air.

In FIGS. 10A and 10B, the acoustic interface device 1004a is cylindrical and has dimensions of 2.0" diameter× 2.0" L, and is made of Teflon® (referred to on the associated graphs of FIGS. 10E and 10F as "white Teflon®"). In FIG. 10A, transducer 1002a is positioned at the center of acoustic interface device 1004a. In FIG. 10B, transducer 1002a is positioned off-centered, near the edge (circumferential periphery) of the acoustic interface device 1004a.

In FIGS. 10C and 10D, the acoustic interface device 1004c is a square plate and has dimensions of 2" H×6" W×6" L, and is made of Teflon® filled with carbon particles (referred to on the associated graphs of FIGS. 10G and 10H as "black Teflon®"). In FIG. 10C, transducer 1002a is positioned at the corner of acoustic interface device 1004c. In FIG. 10D, transducer 1002a is positioned about 1.0" closer to the center (compared to FIG. 10C), but still near the corner, of acoustic interface device 1004c, or about halfway from the corner to the center of acoustic interface device 1004c.

As for the pulse-echo responses, as seen in FIGS. 10E-10H, all four of the waveforms show almost identical pulse shape, amplitude, and travel time of the main reflection echo at about 90 μs, as well as clean tail responses up to around 170 μs. These responses demonstrate dominant p-wave signals and almost no spurious modes and little noise observed, despite different sizes of the acoustic interface device and different positions of the transducer with respect to the acoustic interface device. In particular, it might have been thought that placing the transducer close to the edge of the acoustic interface device would result in increased spurious modes and noise, because it might have been thought that the proximity of the transmitted signal to the edge of the acoustic interface device would result in increased mode conversion due to the transmitted signal increasingly reaching the boundary of the acoustic interface device. The absence of increased spurious modes and noise is understood to attest to the high rate of shear wave attenuation, and perhaps also to the slow shear wave velocity, of the Teflon® composition of the acoustic interface devices.

It will be understood that, with respect to FIGS. 8, 9A-9C and 10A-10H, the dimension L (length) mentioned with reference to a cylindrical acoustic interface device or buffer rod refers to the dimension referred to as height (the y-direction) in the discussion of FIGS. 1 and 3-6 and in the discussion of the cylindrical and cylindrical-type acoustic interface devices of FIG. 2.

Acoustic interface devices such as described herein may provide advantages in ultrasonic measurement. Specifically, providing the acoustic interface device with a material composition having a high shear wave attenuation coefficient $\alpha_S$, a relatively low compressional wave velocity $V_P$, a low shear wave velocity $V_S$, and/or a moderate-to-low compressional wave attenuation coefficient $\alpha_C$, such as are possessed by the specific materials named herein or other compositions, may provide advantages such as the following.

A high shear wave attenuation coefficient $\alpha_S$ may serve to attenuate shear waves generated, e.g., by mode conversion of the acoustic signal hitting the sidewalls (circumferential periphery) of the acoustic interface device. As a result, spurious (trailing) echoes (noise) may be significantly reduced, providing a cleaner response signal of interest (e.g., increased signal-to-noise ratio). The cleaner response signal may permit for increased accuracy of measurement, improved signal processing and interpretation, and increased sensitivity in measurement.

A relatively low compressional wave velocity $V_P$ provides a relatively wide signal processing window before arrival of the second reflection and hence may permit use of an acoustic interface device that is shorter than prior art buffer rods. (This "second reflection" is explained as follows: in FIG. 1, when $r_1$ arrives at transducer 102 at $V_A$, a portion of $r_1$ (not shown) is reflected back in acoustic interface device 104, downward in FIG. 1, toward fluid gap 111. When this portion of $r_1$ reaches the interface between acoustic interface device 104 and fluid gap 111, a part of this portion of $r_1$ is reflected, upward in FIG. 1, back toward transducer 102 and arrives at transducer 102. This portion that arrives at transducer 102 is the "second reflection.") Unlike prior art buffer rods, an acoustic interface device of such short length may fit inside downhole tools. (The dimension of length mentioned here corresponds to the dimension of height in FIGS. 1 and 3-6 and in respect of the cylindrical acoustic interface devices of FIG. 2.)

A low shear wave velocity $V_S$ may serve to eliminate noise in the response signal of interest and thus provide a cleaner signal, since noise in the form of (e.g., mode-converted or other) shear waves may be sufficiently slow so as to interfere only to a small degree with the response signal of interest.

A moderate-to-low compressional wave attenuation coefficient $\alpha_C$ may provide for a strong response signal of interest (e.g., increased signal-to-noise ratio), since the signal may not be greatly weakened prior to being measured.

As seen, all of the above properties generally contribute to achieving a cleaner response signal of interest, e.g., decreased noise (spurious echoes, ringing noise) and improved signal-to-noise ratio, and the attendant benefits.

One application or context of use for an acoustic interface device or measurement cell described herein is logging while tripping (LWT). Using the acoustic interface device or measurement cell, logging can be performed during this time, which otherwise may not be able to be optimally exploited and which may incur a significant cost as suboptimally productive time. In addition, an acoustic interface device or measurement cell described herein may be applicable to well logging tools other than the LWD tool and wireline tool described above.

Figure 11:
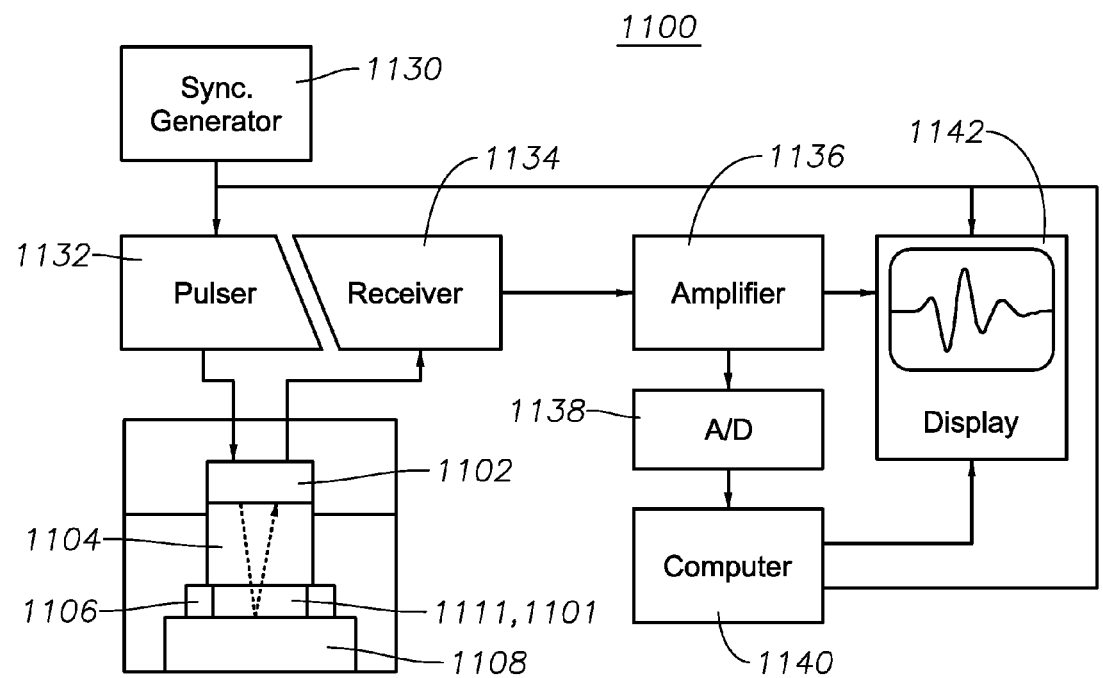
FIG. 11 is a block diagram of an ultrasonic measurement system, according to some embodiments.

FIG. 11 is a block diagram of an ultrasonic measurement system, of which measurement cell 100, 300 or 500 may be a part. Accordingly, ultrasonic measurement system 1100 includes a measurement cell, which is shown schematically in consonance with measurement cell 100 but which may be measurement cell 100, 300 or 500 or another measurement cell. For convenience, only some of the elements of the measurement cell in FIG. 11 are identified, namely, transducer 1102, acoustic interface device 1104, spacer 1106, reflector 1108, fluid gap 1111, and fluid 1101. Acoustic signals (as described above herein) are represented in oversimplified form by the dotted line and arrow. Ultrasonic measurement system 1100 may include a synchronization generator 1130, a pulse generator (pulser) 1132, a receiver 1134, an amplifier 1136, an A/D converter 1138, a computer 1140, and a display 1142. Synchronization generator 1130 may generate trigger signals, e.g., at a high repetition rate, to pulser 1132. In response to these trigger signals, pulser 1132 provides electrical voltage to transducer 1102. In response to this voltage, transducer 1102 generates ultrasonic waves (acoustic signals), e.g., at the same repetition rate. The pulse-echo response (reflected ultrasonic waves, described hereinabove) is received by transducer 1102. In response to the received waves, transducer 1102 provides corresponding electrical voltage to receiver 1134. The received voltage is amplified by amplifier 1136, then converted from analog to digital form by A/D converter 1138, and then processed and analyzed by computer 1140. The amplified voltage is also transmitted from amplifier 1136 to display 1142 (e.g., an oscilloscope), on which it is displayed. The converted digital signal, as well as other associated output information, may also be displayed on display 1142. Computer 1140 may be used for additional functions in ultrasonic measurement system 1100.

To be sure, as will be understood by one of ordinary skill in the art, variants of ultrasonic measurement system 1100 may be employed, e.g., ultrasonic measurement system 1100 may include components in addition to or in substitution for components illustrated here, and may not include all components illustrated here.

An example of one additional component that may be included in ultrasonic measurement system 1100 is a filter, e.g., a high pass filter or a band pass filter (e.g., a 150-550 kHz band pass), which may be used to filter the received acoustic signal in order to obtain a cleaner response signal of interest.

Figure 12:
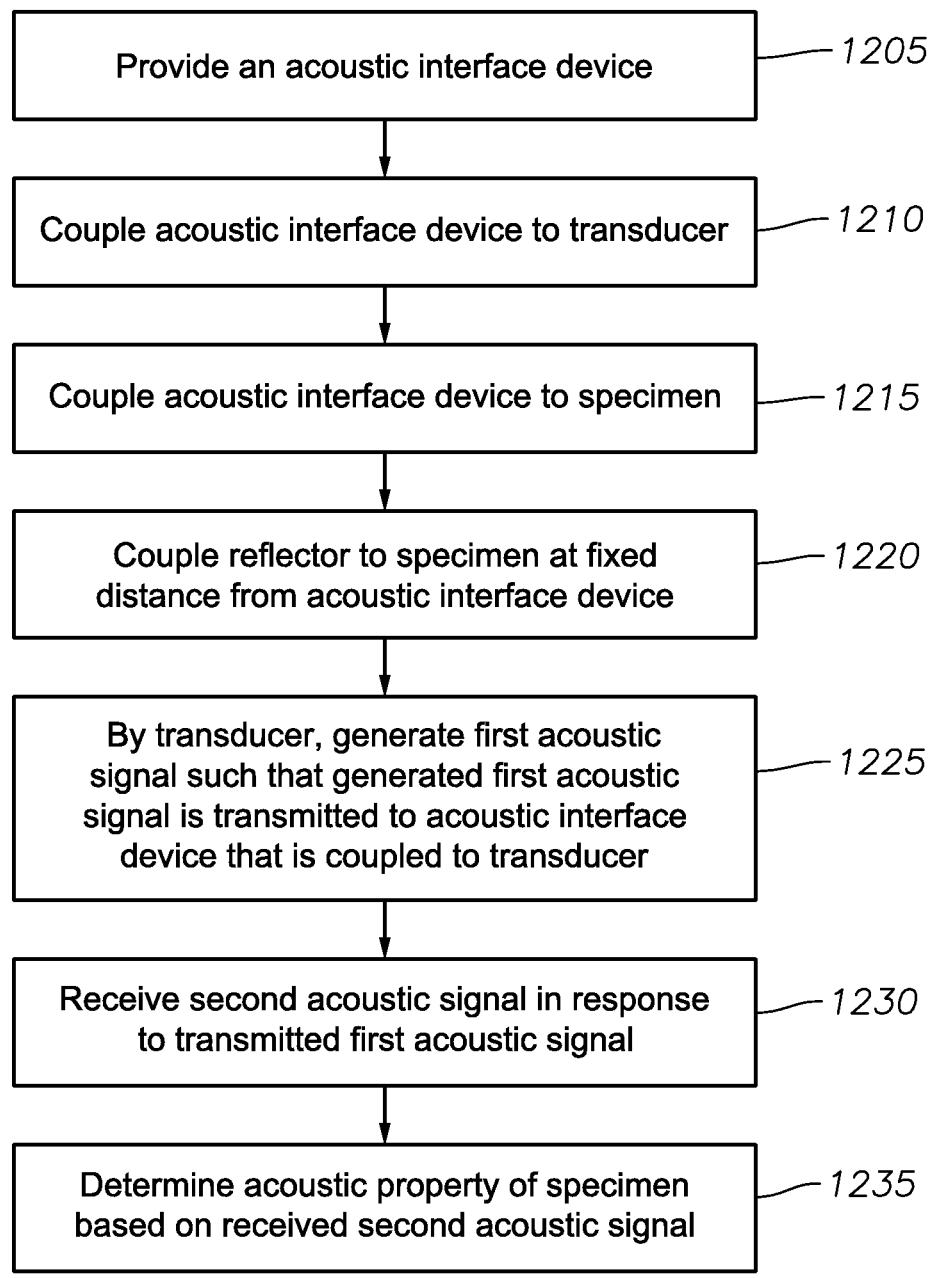
FIG. 12 is a flowchart illustrating a method for performing ultrasonic testing of a specimen using an acoustic interface device, according to some embodiments.

FIG. 12 is a flowchart illustrating an exemplary method 1200 for performing ultrasonic testing of a specimen using an acoustic interface device. According to method 1200, at step 1205, an acoustic interface device is provided. At step 1210, the acoustic interface device is coupled to a transducer. As an example, this coupling may be via a coupling medium, e.g., an oil, a gel, or an epoxy. As another example, this coupling may be achieved by bonding the transducer to the acoustic interface device using, e.g., an epoxy bond. Alternatively, this coupling may be achieved in any suitable manner, as will be understood by one of ordinary skill in the art. At step 1215, the acoustic interface device is coupled to a specimen of interest or material under test. The specimen of interest or material under test may but need not be a fluid. At step 1220, a reflector is coupled to the specimen at a fixed distance from the acoustic interface device. As an example, these couplings to the specimen (steps 1215 and 1220) may be by direct contact, without any coupling medium, or may be achieved in any suitable manner, as will be understood by one of ordinary skill in the art. At step 1225, the transducer generates a first acoustic signal such that the generated first acoustic signal is transmitted to the acoustic interface device that is coupled to the transducer. At step 1230, a second acoustic signal is received in response to the transmitted first acoustic signal. This second acoustic signal (response signal) may be a reflection of the transmitted first acoustic signal, as in a pulse-echo arrangement, and it may be received by the transducer, as described hereinabove. (To avoid possible confusion, it is noted that this second acoustic signal may refer to any one, or collectively to more than one, such reflection, e.g., any one or more of $V_A$, $V_B$, $V_C$ (as depicted) and further reflection echoes (as described in the instant description) with reference to FIGS. 1 and 7. This second acoustic signal is not to be taken as referring exclusively or necessarily to the second of those reflections, namely, $V_B$. Nor is this second acoustic signal to be taken as referring exclusively or necessarily to the "second reflection" described above, that is, in FIG. 1, the portion of $r_1$ that at $V_A$ is reflected back from the transducer toward the fluid gap and then back from the fluid-gap-acoustic-interface-device-interface to the transducer.) In alternative embodiments employing a through-transmission arrangement or a pitch-catch arrangement (described immediately below) rather than a pulse-echo arrangement, this second acoustic signal may be a signal received by the receiver (e.g., receiving transducer) from the specimen in response to the first acoustic signal, which is transmitted by the transmitter (e.g., transmitting transducer) into the specimen. At step 1235, one or more acoustic properties are determined based on the received second acoustic signal(s). Such determination may be based also on or involve additional inputs. It will be understood that further details pertaining to the preceding steps, as well as indications of steps that may be added, substituted, reordered, omitted, or otherwise modified, have been set forth herein and will be appreciated by those of ordinary skill in the art.

One example of such variation of method 1200 would be omission of step 1220. Such variation would be applicable to a through-transmission arrangement or a pitch-catch arrangement rather than a pulse-echo arrangement. Each of a through-transmission arrangement and a pitch-catch arrangement uses two transducers rather than one as may be used in pulse-echo measurement, as described above. In through-transmission arrangement or pitch-catch arrangement, one transducer transmits the acoustic signal into the specimen and another transducer receives the response signal from the specimen. The two transducers may interface the specimen at different locations on the specimen.

While the instant disclosure includes statements that may be understood as offering reasons or explanations for certain phenomena or results, the instant inventors do not wish to be bound by theory.

In light of the principles and example embodiments described and illustrated herein, it will be recognized that the example embodiments can be modified in arrangement and detail without departing from such principles. Also, the foregoing discussion has focused on particular embodiments, but other configurations are also contemplated. In particular, even though expressions such as "in one embodiment," "in another embodiment," or the like are used herein, these phrases are meant to generally reference embodiment possibilities, and are not intended to limit the invention to particular embodiment configurations. As used herein, these terms may reference the same or different embodiments that are combinable into other embodiments. As a rule, any embodiment referenced herein is freely combinable with any one or more of the other embodiments referenced herein, and any number of features of different embodiments are combinable with one another, unless indicated otherwise or so dictated by the description herein in view of the knowledge of one or ordinary skill in the art.

Similarly, although example processes have been described with regard to particular operations performed in a particular sequence, numerous modifications could be applied to those processes to derive numerous alternative embodiments of the present invention. For example, alternative embodiments may include processes that use fewer than all of the disclosed operations, processes that use additional operations, and processes in which the individual operations disclosed herein are combined, subdivided, rearranged, or otherwise altered.

This disclosure may include descriptions of various benefits and advantages that may be provided by various embodiments. One, some, all, or different benefits or advantages may be provided by different embodiments.

In view of the wide variety of useful permutations that may be readily derived from the example embodiments described herein, this detailed description is intended to be illustrative only, and should not be taken as limiting the scope of this invention. What is claimed as the invention, therefore, are all implementations that come within the scope of the following claims, and all equivalents to such implementations.

What is claimed is:

1. A system, comprising:
an acoustic interface device, configured for coupling to a transducer and to a specimen, the acoustic interface device comprising a material composition having a shear wave attenuation coefficient $\alpha_S$ of at least about 5 dB/cm when subjected to an acoustic signal at a frequency between about 200 to 500 kHz.

2. The system of claim 1, wherein the material composition has a compressional wave velocity $V_P$ of at most about 1600 m/s at a temperature between about 150 and 200 degrees Celsius and a pressure between about 20,000 to 35,000 psi.

3. The system of claim 1, wherein the material composition has a shear wave velocity $V_S$ of at most about 1110 m/s at a temperature between about 150 and 200 degrees Celsius and a pressure between about 20,000 to 35,000 psi.

4. The system of claim 1, wherein the material composition has a compressional wave attenuation coefficient $\alpha_C$ of at most about 6 dB/cm when subjected to an acoustic signal at a frequency between about 200 to 500 kHz.

5. The system of claim 1, further comprising a transducer coupled to the acoustic interface device, wherein the transducer is a piezoelectric transducer operable to generate an acoustic signal at least at a frequency between about 200 kHz and 500 kHz in response to an applied electric voltage.

6. The system of claim 5, further comprising a reflector,
wherein the acoustic interface device comprises a proximal end and a distal end,
wherein the acoustic interface device is coupled to the transducer at the proximal end, and the acoustic interface device is coupled to a specimen at the distal end, and
wherein the reflector is coupled to the specimen and disposed a fixed distance away from the distal end.

7. The system of claim 1, wherein
the acoustic interface device comprises a material from the group consisting of: polytetrafluoroethylene (Teflon®), a perfluoroalkoxy alkane (PFA), polycarbonate (Lexan®), and polyether ether ketone (PEEK).

8. The system of claim 7, wherein the acoustic interface device comprises a particle-filled polytetrafluoroethylene (Teflon®) composite.

9. The system of claim 7, further comprising a transducer coupled to the acoustic interface device, wherein the transducer is a piezoelectric transducer operable to generate an acoustic signal at least at a frequency between about 200 kHz and 500 kHz in response to an applied electric voltage.

10. The system of claim 9, further comprising a reflector,
wherein the acoustic interface device comprises a proximal end and a distal end,
wherein the acoustic interface device is coupled to the transducer at the proximal end, and the acoustic interface device is coupled to a specimen at the distal end, and
wherein the reflector is coupled to the specimen and disposed a fixed distance away from the distal end.

11. A method, comprising:
providing an acoustic interface device, coupled to a transducer;
coupling the acoustic interface device to a specimen;
by the transducer, generating a first acoustic signal, such that the generated first acoustic signal is transmitted to the acoustic interface device; and
receiving a second acoustic signal in response to the transmitted first acoustic signal,
wherein the acoustic interface device comprises a material composition having a shear wave attenuation coefficient $\alpha_S$ of at least about 5 dB/cm when subjected to an acoustic signal at a frequency between about 200 to 500 kHz.

12. The method of claim 11, further comprising:
coupling a reflector to the specimen at a fixed distance from the acoustic interface device.

13. The method of claim 11, further comprising:
determining an acoustic property of the specimen based on the received second acoustic signal.

14. The method of claim 11, wherein the material composition of the acoustic interface device has at least one property from the group consisting of: having a compressional wave velocity $V_P$ of at most about 1600 m/s at a temperature between about 150 and 200 degrees Celsius and a pressure between about 20,000 to 35,000 psi; having a shear wave velocity $V_S$ of at most about 1110 m/s at a temperature between about 150 and 200 degrees Celsius and a pressure between about 20,000 to 35,000 psi; and having a compressional wave attenuation coefficient $\alpha_C$ of at most about 6 dB/cm when subjected to an acoustic signal at a frequency between about 200 to 500 kHz.

15. The method of claim 11, wherein the specimen is a liquid.

16. The method of claim 11,
wherein the acoustic interface device comprises a material from the group consisting of: polytetrafluoroethylene (Teflon®), a perfluoroalkoxy alkane (PFA), polycarbonate (Lexan®), and polyether ether ketone (PEEK).

17. The method of claim 16, wherein the acoustic interface device comprises a particle-filled polytetrafluoroethylene (Teflon®) composite.

18. The method of claim 16, further comprising:
coupling a reflector to the specimen at a fixed distance from the acoustic interface device.

19. The method of claim 16, further comprising:
determining an acoustic property of the specimen based on the received second acoustic signal.

20. The method of claim 16, wherein the specimen is a liquid.

* * * * *